(12) United States Patent
Jablonski

(10) Patent No.: US 11,511,065 B2
(45) Date of Patent: Nov. 29, 2022

(54) PATIENT INTERFACE DEVICE WITH AUTO-ADJUSTING CUSHION

(71) Applicant: KONINKLIJKE PHILIPS N. V., Eindhoven (NL)

(72) Inventor: Gregory John Jablonski, Butler, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 157 days.

(21) Appl. No.: 16/245,614

(22) Filed: Jan. 11, 2019

(65) Prior Publication Data

US 2019/0143065 A1    May 16, 2019

Related U.S. Application Data

(60) Continuation of application No. 15/437,091, filed on Feb. 20, 2017, now Pat. No. 10,213,570, which is a
(Continued)

(51) Int. Cl.
| | | |
|---|---|---|
| *A61M 16/06* | (2006.01) | |
| *A61M 16/00* | (2006.01) | |
| *A61M 16/08* | (2006.01) | |

(52) U.S. Cl.
CPC .... *A61M 16/0622* (2014.02); *A61M 16/0057* (2013.01); *A61M 16/06* (2013.01);
(Continued)

(58) Field of Classification Search
CPC .... A61M 16/00; A61M 16/0003–0012; A61M 16/06–0694; A61M 16/08–0883;
(Continued)

(56) References Cited

U.S. PATENT DOCUMENTS 5,662,101 A * 9/1997 Ogden .............. A61M 16/0683
128/912
5,921,239 A * 7/1999 McCall ............. A61M 16/0605
128/205.25
(Continued)

FOREIGN PATENT DOCUMENTS

| CN | 102458547 A | 5/2012 |
|---|---|---|
| EP | 2022528 A2 | 11/2009 |

(Continued)

OTHER PUBLICATIONS

Philips Respironics Masks for CPAP/BiPAP/BiLEVEL, Jun. 21, 2010 http://www.directhomemedical.com/index-respironics-products.html.
(Continued)

*Primary Examiner* — Margaret M Luarca
(74) *Attorney, Agent, or Firm* — Michael W. Haas

(57) ABSTRACT

A patient interface device includes a frame member and a cushion having a main body, a sealing portion, and first and second posts extending from the main body. The frame member defines a first orifice and a second orifice. The first post of the cushion is rotatably received within the first orifice and the second post is rotatably received within the second orifice in a manner that permits the cushion to rotate relative to the frame member.

4 Claims, 7 Drawing Sheets

Related U.S. Application Data division of application No. 13/818,181, filed as application No. PCT/IB2011/053645 on Aug. 18, 2011, now Pat. No. 9,597,474.

(60) Provisional application No. 61/378,101, filed on Aug. 30, 2010.

(52) U.S. Cl.
CPC .... *A61M 16/0605* (2014.02); *A61M 16/0666* (2013.01); *A61M 16/0683* (2013.01); *A61M 16/0816* (2013.01); *A61M 16/0875* (2013.01); *A61M 2016/0661* (2013.01); *A61M 2205/0216* (2013.01); *A61M 2210/0618* (2013.01)

(58) Field of Classification Search
CPC ...... A61M 16/0875; A61M 16/20–029; A61M 2016/0015–0042; A61M 16/0622; A61M 16/0605; A61M 16/0683; A61M 16/0816; A62B 7/00; A62B 7/04; A62B 7/14; B63C 11/12; B63C 11/18

See application file for complete search history.

(56) References Cited

U.S. PATENT DOCUMENTS

| | | | |
|---|---|---|---|
| 6,631,718 B1 * | 10/2003 | Lovell | A61M 16/0683 128/207.13 |
| 7,997,267 B2 | 8/2011 | Ging | |
| 9,925,349 B2 | 3/2018 | Jablonski | |
| 2004/0226566 A1 | 11/2004 | Gunaratnam | |
| 2006/0060200 A1 * | 3/2006 | Ho | A61M 16/0683 128/206.11 |
| 2006/0207599 A1 * | 9/2006 | Busch | A61M 16/0816 128/206.24 |
| 2007/0028919 A1 | 2/2007 | Ho | |
| 2007/0044804 A1 | 3/2007 | Matula | |
| 2009/0044808 A1 * | 2/2009 | Guney | A61M 16/0825 128/207.18 |
| 2009/0101141 A1 * | 4/2009 | Ging | A62B 18/084 128/201.22 |
| 2010/0012129 A1 | 1/2010 | Kwok | |

FOREIGN PATENT DOCUMENTS

| | | |
|---|---|---|
| JP | 2004000571 A | 1/2004 |
| JP | 2005537904 A | 12/2005 |
| JP | 2010119895 A | 6/2010 |
| WO | WO2004022145 A1 | 3/2004 |
| WO | WO2008106716 A1 | 9/2008 |
| WO | WO2009052560 A1 | 4/2009 |
| WO | WO2010135785 A1 | 12/2010 |

OTHER PUBLICATIONS

CPAP Mask, Jun. 21, 2010 http://search.cpapxchange.com/cpap-mask-list.

* cited by examiner

PATIENT INTERFACE DEVICE WITH AUTO-ADJUSTING CUSHION

CROSS REFERENCE TO RELATED APPLICATION

This patent application is a Continuation of U.S. patent application Ser. No. 15/437,091, filed Feb. 20, 2017, which claims the priority benefit under 35 U.S.C. § 119(e) of U.S. patent application Ser. No. 13/818,181, filed Feb. 21, 2013, now U.S. Pat. No. 9,597,474, granted Mar. 21, 2017, which claims benefit under 35 U.S.C. § 371 of International Application No. PCT/IB32011/053645 filed on Aug. 18, 2011, which claims the priority benefit under 35 U.S.C. § 119(e) of U.S. Provisional Application No. 61/378,101 filed on Aug. 30, 2010, the contents of which are herein incorporated by reference.

BACKGROUND OF THE INVENTION

1. Field of the Invention

The present invention relates to patient interface devices for communicating a flow of gas with an airway of a user, and, in particular, to a patient interface device having a structure that includes controlled flexing and auto-adjustment of a cushion relative to a frame.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Patients that that require pressure support therapy are often confronted with the problem of finding a suitable patient interface device. In finding a suitable patient interface device, such patients frequently struggle with issues relating to the seal and stability of the patient interface device, the comfort of the patient interface device, the size/weight of the patient interface device, and the sizing of the patient interface device. These challenges, if not addressed properly, can compromise the patient's compliance with the prescribed therapy.

More specifically, during the night, the stability of a mask seal will be challenged by the patient moving about in his or her bed. The changing head position can lead to air delivery hose torque and general interference with other objects (e.g. pillows, sheets, blankets, etc.). Thus, stability, and consequently seal, is a challenge for any patient interface device in the market.

In addition, patient comfort is an important factor, and can be negatively impacted in many ways. For example, over-tightening of the headgear (to compensate for lack of seal and stability) can increase pressure on the face and head, which in turn can result in pressure points and/or skin breakdown. Other components of the patient interface device (e.g. straps, frames, headgear, etc.) can also add discomfort for the patient because the geometry of such components can conflict with facial structures.

Furthermore, the general weight of the patient interface device can negatively impact a patient's experience by causing additional facial pressure or compounding over-tightening issues. Patient interface device weight can also negatively affect the seal and stability. Certain patients also have problems with a patient interface device interfering with his or her line of sight, and overall patient interface device size has been known to cause claustrophobia is some patients.

Finally, properly sizing a patient interface device can be difficult because facial structures vary greatly among patients. Not all patient interface devices are able to accommodate this range of differences, thus requiring either more sizes/variations or not providing an optimal fit for the majority of the user population.

SUMMARY OF THE INVENTION

Accordingly, it is an object of the present invention to provide a patient interface device that overcomes the shortcomings of conventional patient interface device. This object is achieved according to one embodiment of the present invention by providing a patient interface device that includes a frame member and a cushion having a main body, a sealing portion coupled to the main body, and a first post extending from a first side of the main body and second post extending from a second side of the main body. The frame member defines a first orifice and a second orifice. The first post of the cushion is rotatably received within the first orifice and the second post is rotatably received within the second orifice in a manner that permits the cushion to rotate relative to the frame member.

In another embodiment, a method of adjusting a patient interface device is provided that includes donning a patient interface device as just described, and causing the cushion to rotate relative to the frame member when the sealing portion is engaged with the face of the patient.

In still another embodiment, a cushion for a patient interface device includes a main body, a sealing portion coupled to the main body, a first post extending from a first side of the main body and structured to be rotatably received within a first orifice of a frame member of the patient interface device, and a second post extending from a second side of the main body and structured to be rotatably received within a second orifice of a frame member of the patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
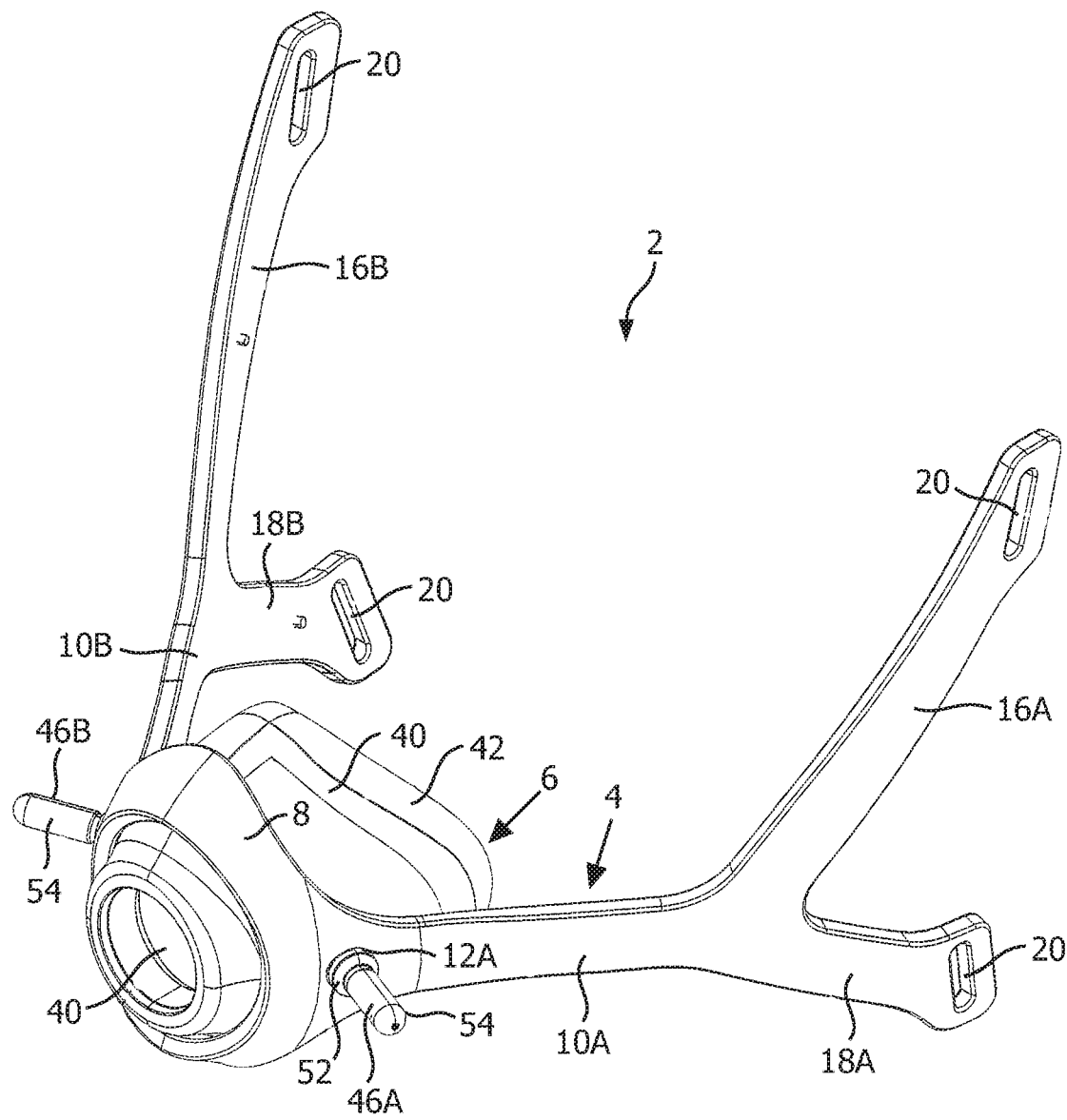
FIG. 1 is a front perspective view of a patient interface device according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 9:
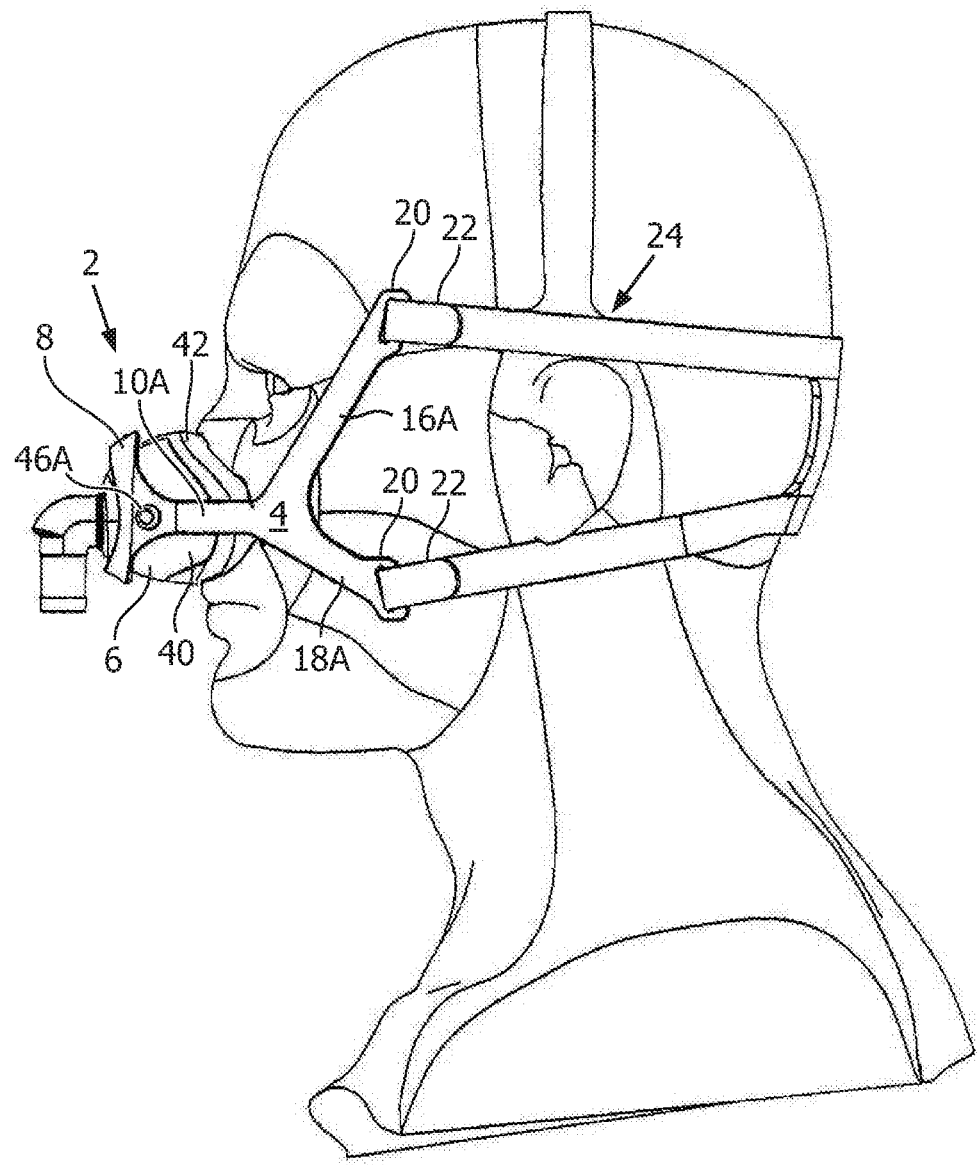
FIG. 9 is a side view and FIG. 10 is a perspective view showing the patient interface device of FIG. 1 attached to a patient.
Figure 10:
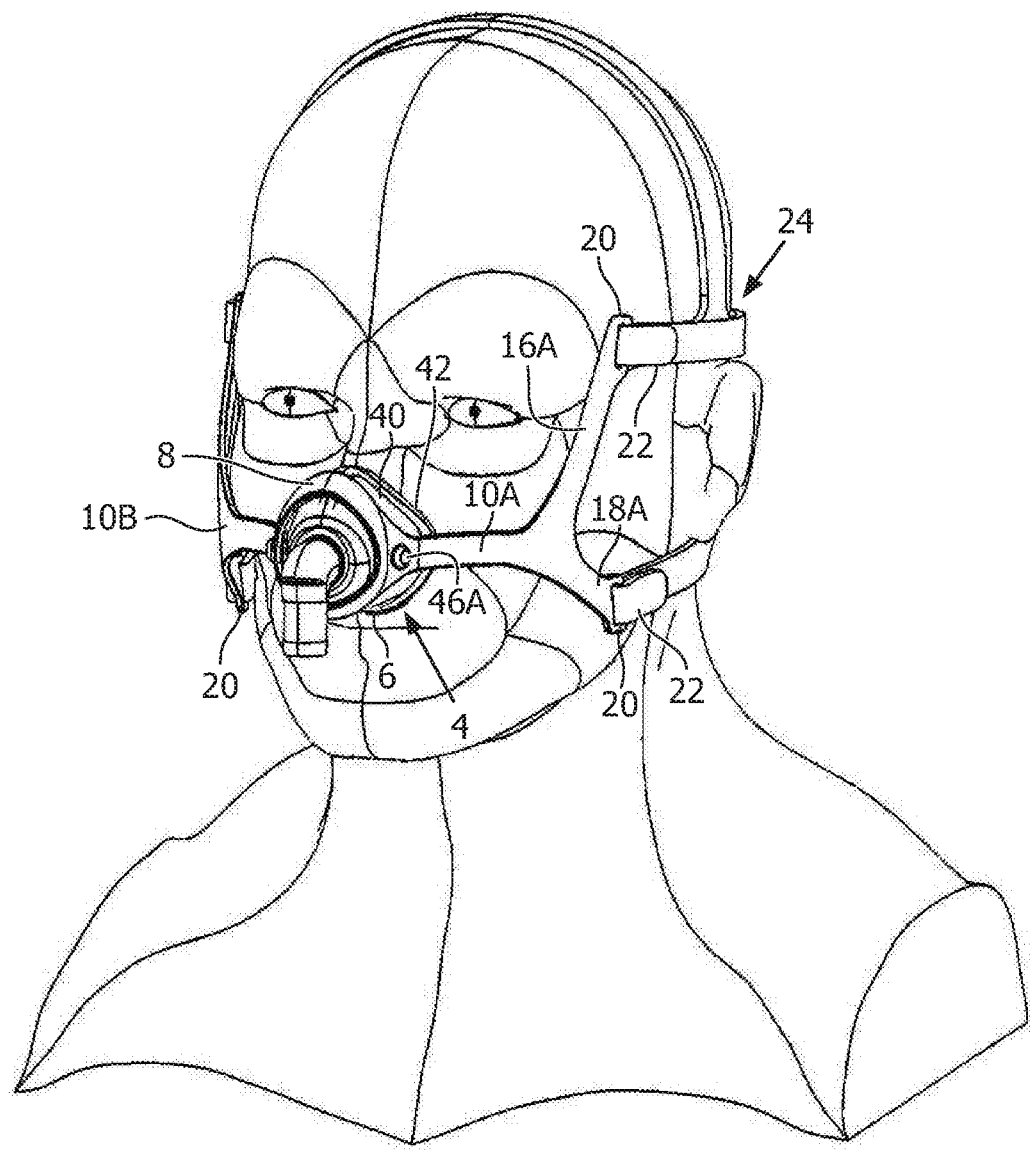

FIG. 1 is a front perspective view of a patient interface device 2 according to an exemplary embodiment of the present invention. FIG. 9 is a side view and FIG. 10 is a front perspective view showing patient interface device 2 attached to a patient. Patient interface device 2 includes a frame member 4 and a cushion 6 coupled to the frame member, each of which is described in greater detail herein.

Figure 2:
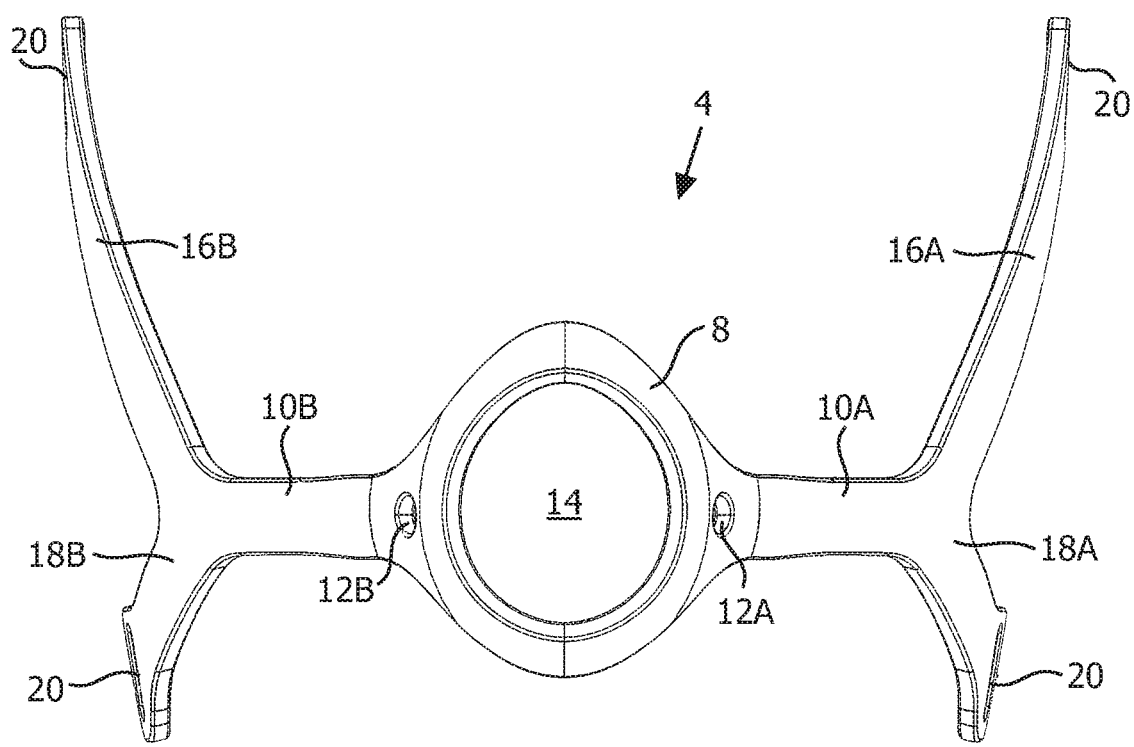
FIGS. 2, 3, 4, and 5 are front, rear, top and side elevational views, respectively, of a frame member of the patient interface device of FIG. 1.
Figure 3:
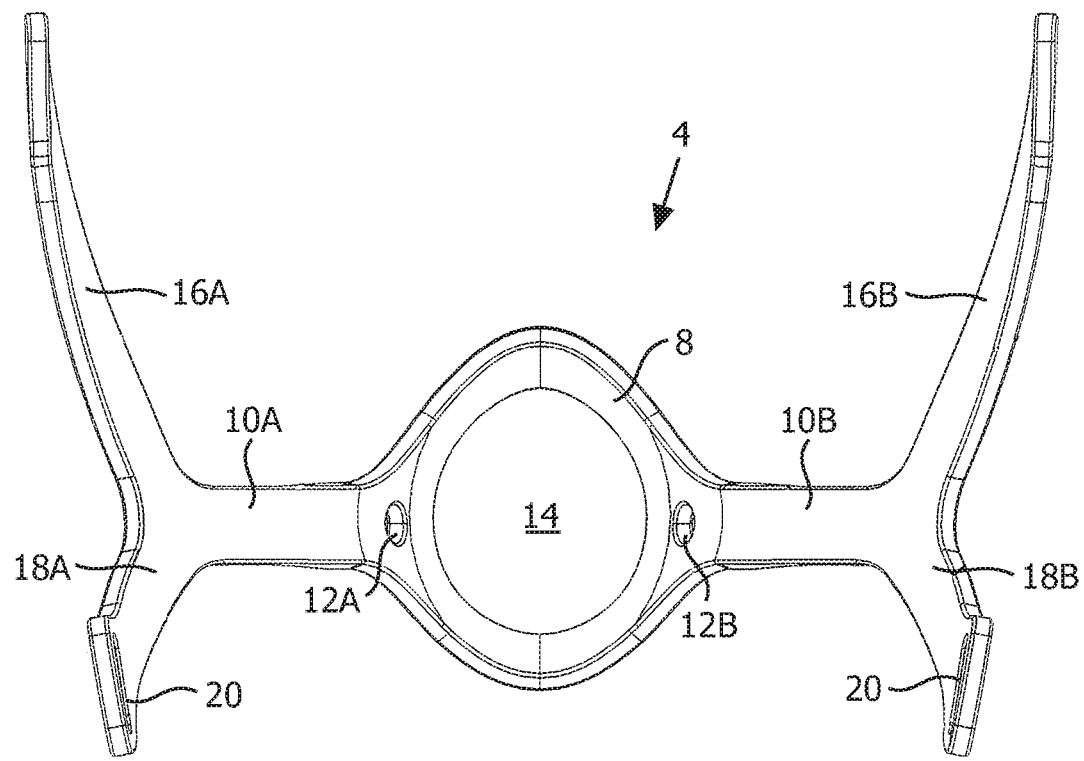

FIGS. 2, 3, 4, and 5 are front, rear, top, and side elevational views, respectively, of frame member 4 of patient interface device 2. Frame member 4 includes a generally annular central member 8 having first and second main arms 10A, 10B extending outwardly from opposites sides thereof. Main arm 10A includes orifice 12A extending therethrough, and main arm 10B includes orifice 12B extending therethrough. In the exemplary embodiment, orifices 12A, 12B are positioned at a location on main arms 10A, 10B adjacent central member 8. The purpose of orifices 12A, 12B is described in detail elsewhere herein. In addition, as seen in FIGS. 2 and 3, central member 8 defines a central orifice 14.

Frame member 4 further includes a first branching member 16A extending upwardly at an angle from main arm 10A and a first branching member 16B extending upwardly at an angle from main arm 10B. In one particular, non-limiting embodiment, first branching members 16A, 16B extend upwardly from the respective main arm 10A, 10B at an angle of about 60 degrees, although other angles are also possible. Furthermore, frame member 4 also includes a second branching member 18A extending downwardly at an angle from main arm 10A and a second branching member 18B extending downwardly at an angle from main arm 10B. In one particular, non-limiting embodiment, second branching members 18A, 18B extend downwardly from the respective main arm 10A, 10B at an angle of about 30 degrees], although other angles are also possible. Also in one particular, non-limiting embodiment, main arms 10A and 10B extend for about 55-60 mm from the center of orifices 12A, 12B to the inner angles formed between the branching members 16A and 18A and 16B and 18B, respectively.

Moreover, as seen in FIGS. 1-5, the distal end of each of first branching member 16A, 16B and second branching member 18A, 18B includes a respective loop member 20 for receiving a respective strap 22 of headgear assembly 24 (FIGS. 9 and 10). In the exemplary embodiment, frame member 4 is made of a thermoplastic or thermoset material.

Figure 6:
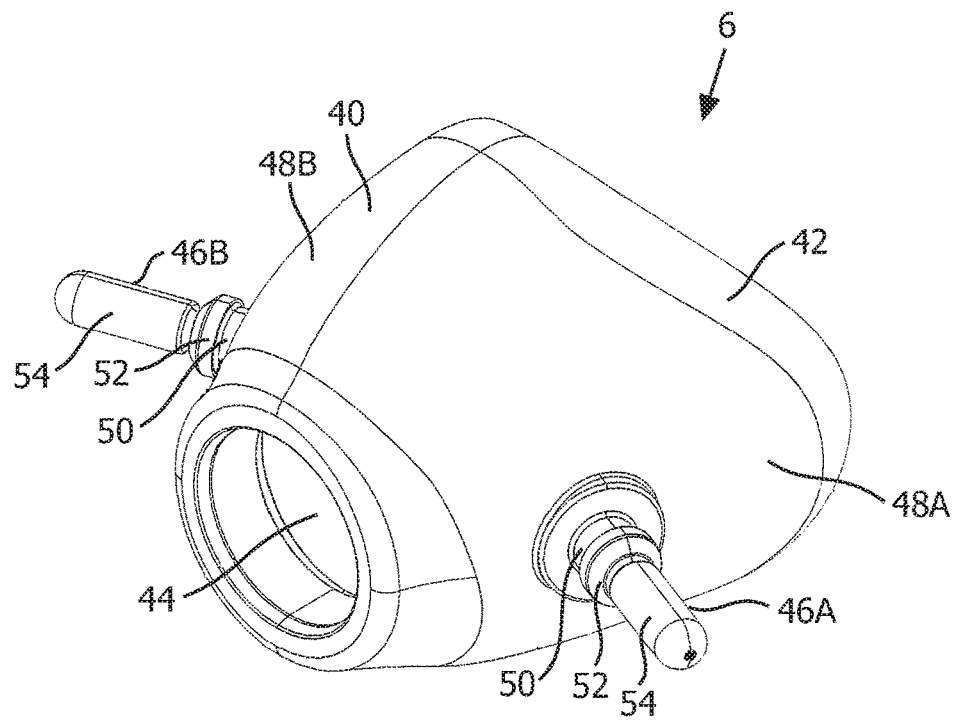
FIGS. 6, 7, and 8 are front isometric, front elevational and rear elevational views, respectively, of the cushion of the patient interface device of FIG. 1.
Figure 7:
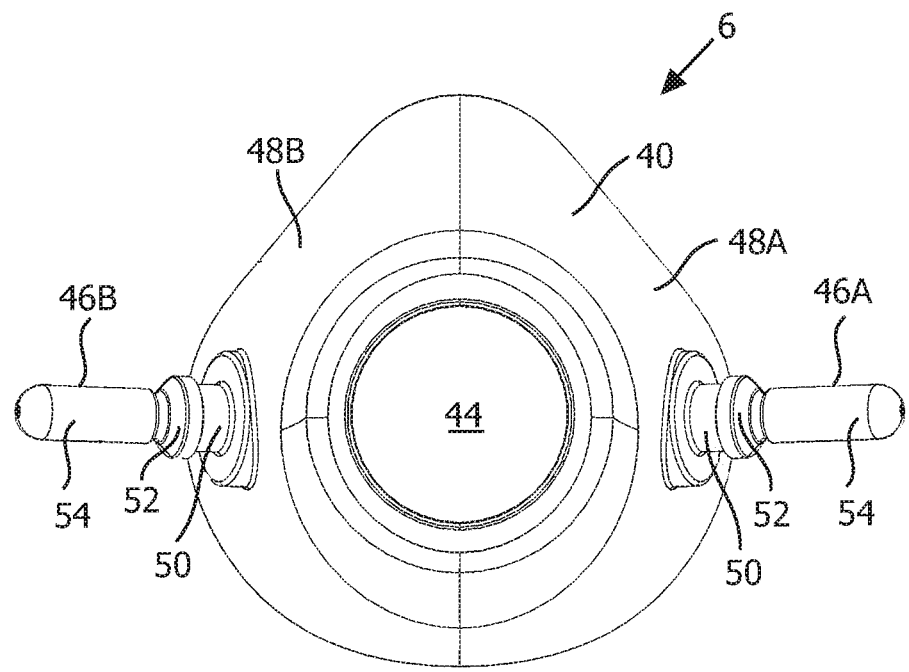
Figure 8:
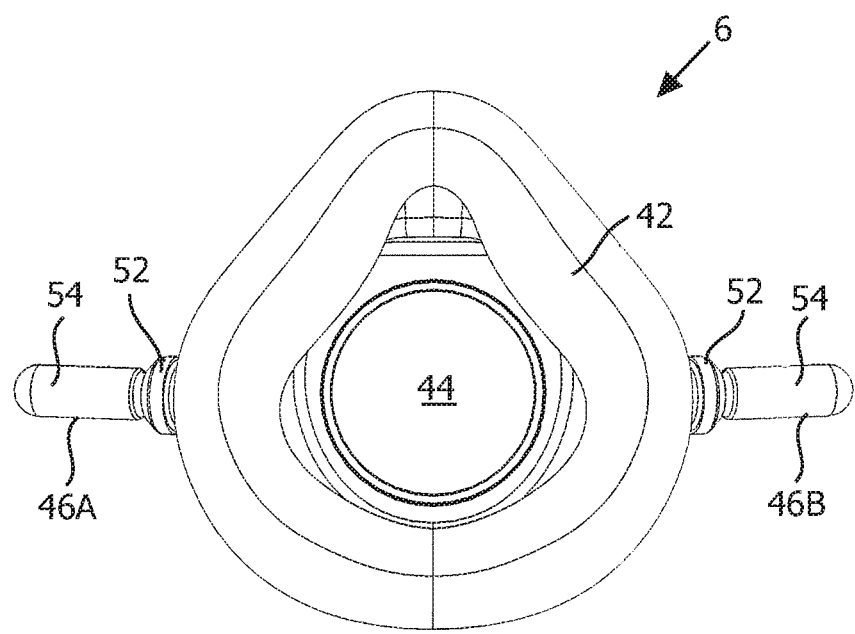

FIGS. 6, 7, and 8 are front isometric, front elevational and rear elevational views, respectively, of cushion 6 of patient interface device 2. In the exemplary embodiment, cushion 6 is defined from a unitary piece of soft, flexible, cushiony, elastomeric material, such as, without limitation, silicone, an appropriately soft thermoplastic elastomer, a closed cell foam, or any combination of such materials. Cushion 6 includes a main body portion 40 having a sealing portion 42 coupled to a first end thereof. Sealing portion 42 is structured to form a seal against a face of the patient. In the illustrated embodiment, cushion 6 is in the form of a nasal mask. However, other types of patient sealing assemblies, such as a nasal/oral mask, nasal cannula, or a nasal cushion, which facilitate the delivery of the flow of breathing gas to the airway of a patient, may be substituted for cushion 6 while remaining within the scope of the present invention.

In addition, main body portion 40 defines an orifice 44 at the second end thereof opposite the first end. Orifice 44 is structured to enable cushion 6 to be fluidly coupled to a fluid connector such as an elbow conduit, which in turn is fluidly coupled a pressure generating device such as a ventilator or a CPAP machine through a gas delivery hose.

Cushion 6 further includes generally cylindrically shaped posts 46A and 46B extending from first and second sides 48A and 48B, respectively, of main body 40. Each post 46A, 46B is positioned about midway between the first and second end of cushion 6. In addition, each post 46A, 46B includes an inner cylindrical portion 50, an enlarged portion 52, and an outer cylindrical portion 54.

When patient interface device 2 is assembled, the second end of main body 40 is inserted through central orifice 14 defined by central member 8. In addition, post 46A is inserted through orifice 12A and post 46B is inserted through orifice 12B. More specifically, as seen in FIG. 1, in each case, outer cylindrical portion 54 and enlarged portion 52 are inserted through the respective orifice 12A, 12B such that each enlarged portion 52 rests against the outer surface of main arm 10A, 10B and prevents outer cylindrical portion 54 from sliding back through orifice 12A, 12B. In addition, each inner cylindrical portion 50 is able to turn within the respective orifice 12A, 12B.

The branching nature of the sides of frame member 4, giving it a "T" or "Y" shape, allows for flexing of frame member 4 in certain directions while at the same time limiting flexing in other directions. In particular, main arms 10A, 10B are able to flex in the directions shown by the arrows in FIG. 4 (i.e., parallel to the top and bottom surface of main arms 10A, 10B), but are not able to freely flex in a direction transverse to the longitudinal axis thereof (i.e., perpendicular to the top and bottom surface of main arms 10A, 10B).

Figure 4:
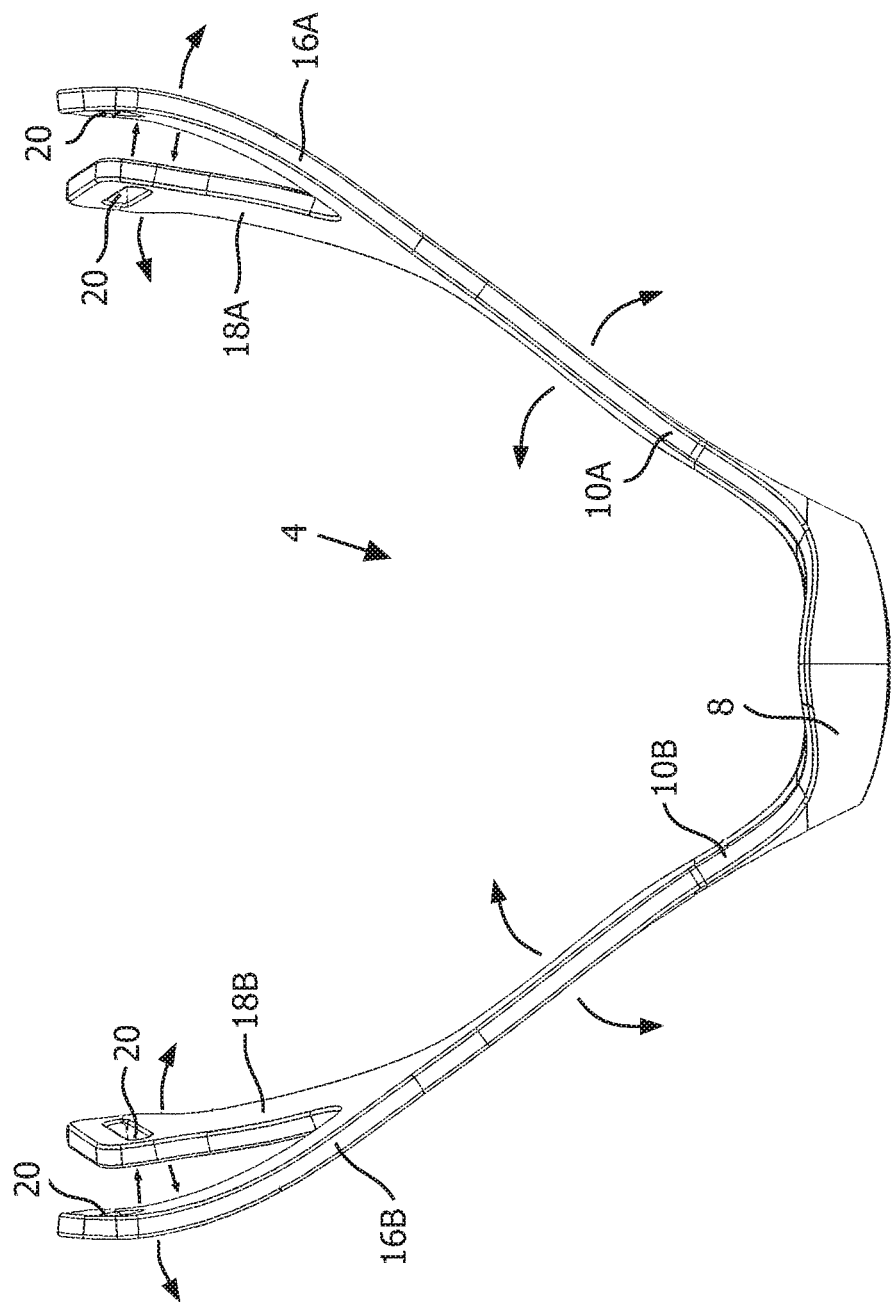
Figure 5:
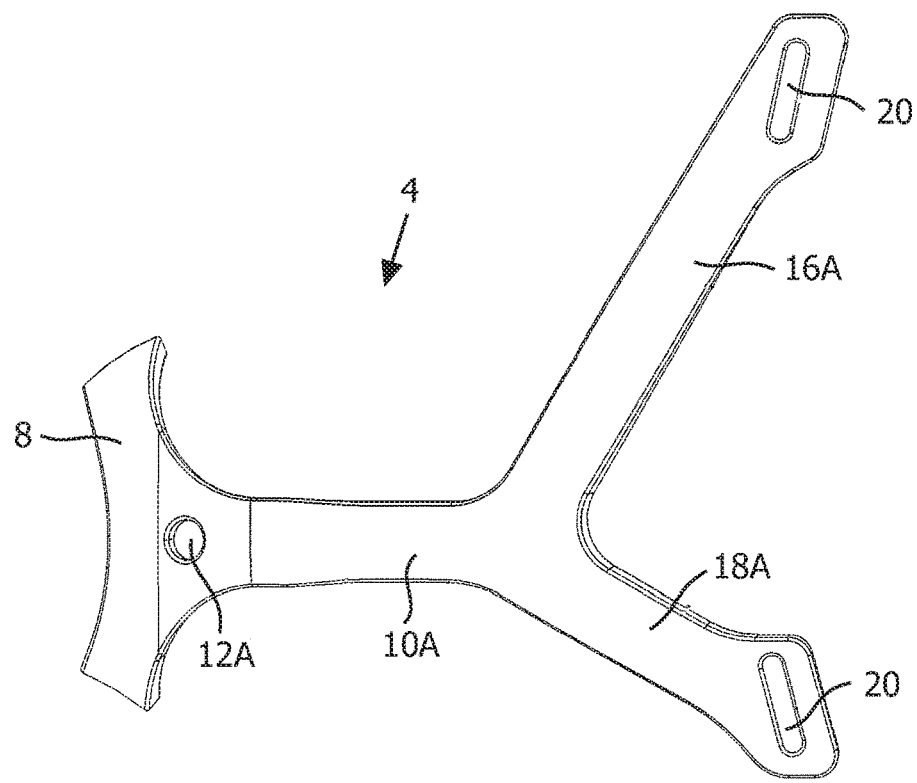

In addition, each of the first branching members 16A, 16B and second branching member 18A, 18B are able to flex independently of one another in the directions shown by the arrows in FIG. 4 (i.e., parallel to the top and bottom surface of the branching members), but are not able to freely flex in a direction transverse to the longitudinal axis thereof (i.e., perpendicular to the top and bottom surface of the branching members). This controlled flexing addresses several issues present in the prior art relating to seal, stability and comfort discussed elsewhere herein, as it passively accommodates for many facial and head geometries to allow for optimal fit and comfort. The branched structure of frame member 4 also increases the stability of patient interface device 2 through patient movement and hose torque, which provides an optimal seal for the patient.

The selection of the material for frame member 4 in conjunction with the geometry of frame member 4 as described herein allows for flexing to accommodate the vast variation in patient facial structures and head dimensions. In the exemplary embodiment, the material will be soft enough to provide for flexing in the desired directions as described herein, but rigid enough to limit the flexing in non-desired directions as described herein. Also, the geometry will, in the exemplary embodiment, allow for accommodation of not only the temple, cheek and jaw regions, but will also cover varying head sizes and nose locations. The geometry of portions of frame member 4 may, for example, vary in thickness, existence of ribs or other structures, and/or general dimensioning to accommodate differences in flexing due to the material properties, but will maintain the branching shape described herein.

Other alternative methods of controlling the direction of flexing of frame ember 4 in the various directions can be accomplished with the use of structures such as hinges incorporated therein. The hinge can be accomplished in a number of different ways, such as with mechanical interlocking (removable or permanent) or over molding with materials such as silicone or other elastomers.

Furthermore, the branching nature of the sides of frame member 4, giving it the "T" or "Y" shape discussed above, moves the mounting or anchor point (i.e., loops 20) for patient interface device 2 on the head of the patient through headgear assembly 24 further back along the side of the head. Typical mounting locations of nasal masks have been on one or many of the following: cheeks, forehead, and chin. By moving the mounting point away from the front of the face, it improves the issues with claustrophobia and line of sight infringement. It also limits the pressure and potential discomfort from over-tightening to the less sensitive areas of the face.

In addition, the interaction between posts 46A, 46B and orifices 12A, 12B provide the connection point for cushion 6 to frame 4. That connection point provides for a passive auto-adjustment mechanism for cushion 6, as posts 46A and 46B, and thus cushion 6, are able to rotate relative to frame member 4. In the exemplary embodiment, each post 46A, 46B has enough interference with frame member 4 to limit excessive rotation but not enough resistance to prevent auto-adjustment. Also in the exemplary embodiment, the cylindrical shape of each post 46A, 46B, as opposed to an oval or other geometry, allows for an infinite amount of positions instead of discrete positioning. This auto-adjusting feature optimizes the angle of engagement of cushion 6 to the face of the patient and increases the chance for an optimal seal across many patient faces of differing sizes and shapes. It also decreases the chance of undue pressure along the sealing portion 42 of cushion 6 on the face (particularly the upper lip) of the patient. Lastly, this auto-adjusting feature provides the ability of cushion 6 to adjust during patient movement, thus increasing stability throughout the night.

The present invention contemplates that posts 46A, 46B are formed from the same material as cushion 6. In this embodiment, the cushion and posts may be molded as a unitary structure to simplify manufacture. The present invention also contemplates that the posts may be formed from a different material (or combination of materials that differ) from cushion 6. The present invention contemplates that the post are flexible and/or the connection of the posts to the cushion is a flexing joint to provide even further passive adjustment of the cushion relative to frame member 4.

Thus, the combination of the flexing frame member 4 and the auto-adjusting cushion 6 allows for placement of frame member 4 on the face to vary in order to meet the individual patient's needs. This allows an opportunity for the patient to alleviate any possible pressure points and/or optimize seal and stability. In addition, the mounting point of cushion 6 to frame member 4 has been moved closer to the patient's face, which increases the stability of patient interface device 2 by moving the fulcrum closer to the patient's face (moment arm decreases). It also lessens the overall profile of patient interface device 2, creating a lower profile that improves overall size and appearance.

Moreover, while cushion 6 has, for illustrative purposes, been described herein in connection with the particular flexing frame member 4, it is to be understood that the present invention is not limited to use with such a frame member and that cushion 6 may be used with and coupled to other, alternative frame members having alternative configurations and shapes without departing from the scope of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device comprising:
    a frame member, the frame member being a unitary structure and including:
        a generally arcuate central member,
        a first main arm having a first end coupled to a first end of the central member, and a second end, a second main arm having a first end coupled to a second end of the central member, and a second end, a first branching member having a first end coupled to the second end of the first main arm, and a second end, a second branching member having a first end also coupled to the second end of the first main arm, and a second end, such that the first branching member, the second branching member, and the first main arm define a first "Y" shape, a third branching member having a first end coupled to the second end of the second main arm, and a second end, and a fourth branching member having a first end also coupled to the second end of the second main arm, and a second end, such that the third branching member, the fourth branching member, and the second main arm define a second "Y" shape, and wherein a headgear connector is provided at a distal end of each of the first, second, third, and fourth branching members;

a cushion having a main body, a sealing portion provided at a first end of the cushion and a second end opposite the sealing portion that defines a fluid coupling orifice, wherein the sealing portion is structured to engage and seal against a face of a user of the patient interface device when the patient interface assembly is donned by the user, wherein the second end of the cushion including the fluid coupling orifice is inserted through a central orifice of the central member of the frame member such that fluid coupling orifice and the sealing portion are positioned on opposite sides of the central member;

an elbow member having a first end and a second end, wherein the first end of the elbow member is selectively received within the fluid coupling orifice in a manner wherein the elbow member directly contacts the second end of the cushion;

a flexible conduit coupled to the second end of the elbow member; and a headgear assembly including a plurality of connecting straps selectively coupled to the headgear connectors provided at the second end of the first branching member, the second end of the second branching member, the second end of the third branching member, and the second end of the fourth branching member, an over the head strap coupled to two of the connecting straps, and a back strap coupled to the connecting straps, wherein when the patient interface assembly is donned by a user:

the first arm member spans at least a portion of a first side of the user's face and the second arm member spans at least a portion of a second side of the user's face opposite the first side of the user's face, the second end of the first branching member and the second end of the third branching member are positioned above and forward the user's ears, and the second end of the second branching member and the second end of the fourth branching member are positioned below and forward the user's ears.

2. The patient interface device according to claim 1, wherein the cushion main body is a rigid member and the sealing portion is a flexible member.

3. The patient interface device according to claim 1, wherein the elbow member is rotatable relative to the cushion.

4. The patient interface device according to claim 1, wherein at least one of the connecting straps is selectively connected to a respective headgear connector via a hook-and-loop fastener.

* * * * *